United States Patent [19]

Eckstein et al.

[11] 4,392,389

[45] Jul. 12, 1983

[54] SAMPLING TUBE HAVING CLOSING CAPS

[75] Inventors: Wolfgang Eckstein, Sereetz; Horst Rabenecker, Klein Parin; Jürgen Behnke, Lubeck, all of Fed. Rep. of Germany

[73] Assignee: Drägerwerk Aktiengesellschaft, Fed. Rep. of Germany

[21] Appl. No.: 299,078

[22] Filed: Sep. 3, 1981

[30] Foreign Application Priority Data

Oct. 7, 1980 [DE] Fed. Rep. of Germany ....... 3037826

[51] Int. Cl.³ .................. G01N 1/00; B65D 21/02; B65D 85/20; B01L 3/12
[52] U.S. Cl. .................. 73/864.91; 206/443; 206/534.1; 206/602; 206/820; 215/227; 215/228; 215/253; 220/23.4; 220/23.8
[58] Field of Search .............. 73/864.91; 422/88, 102, 422/104; 215/227, 228, 230, 250, 253, 306; 220/23.2, 23.4; 206/334, 443, 528, 534, 534.1, 538, 602, 820; 604/403, 404, 410, 413

[56] References Cited

U.S. PATENT DOCUMENTS

| 2,808,926 | 10/1957 | Drake et al. | 206/820 |
| 3,295,710 | 1/1967 | Marchant | 206/820 |
| 3,907,505 | 9/1975 | Beall | 422/102 |
| 3,952,873 | 4/1976 | Pampauch | 206/528 |
| 3,954,176 | 5/1976 | Haytayan | 206/820 |
| 4,007,639 | 2/1977 | Haeckel | 73/864.91 |
| 4,155,479 | 5/1979 | Leichti et al. | 220/23.4 |

Primary Examiner—S. Clement Swisher
Attorney, Agent, or Firm—McGlew and Tuttle

[57] ABSTRACT

A sampling tube arrangement of the type having elongated sampling tubes with closing caps made of elastic plastic material is disclosed in which a plurality of closing caps are joined one to another through severable webs connecting adjacent closing caps. Each cap is provided with a plug-in connection comprising a male part on one side and a female part on the other side to provide a reconnecting mechanism for reconnecting the closed tubes after the sampling has been completed.

3 Claims, 4 Drawing Figures

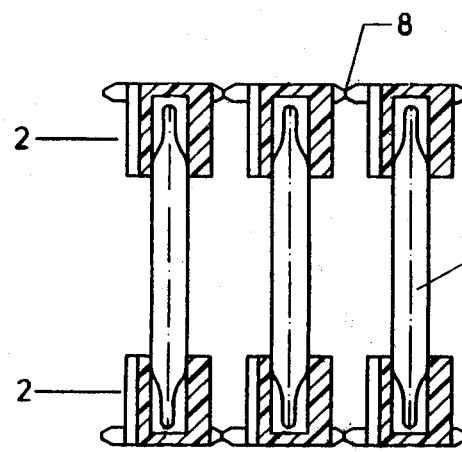
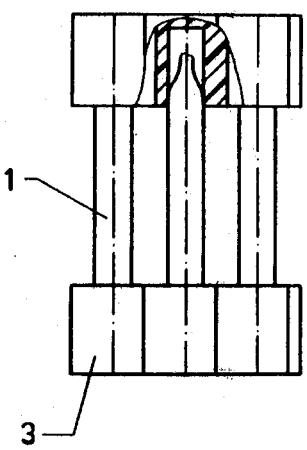
Fig.1          Fig.4
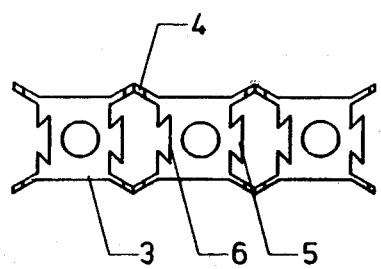
Fig.2
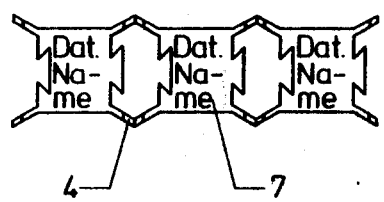
Fig.3

SAMPLING TUBE HAVING CLOSING CAPS

FIELD AND BACKGROUND OF THE INVENTION

The invention relates in general to a gas sampling tube, and more particularly, to a sampling tube with closing caps made of an elastic material.

Sampling tubes are used to obtain a gas sample for subsequent laboratory analysis and are, accordingly, distinguished from tubes known as indicator tubes, which are designed for in situ operations. Thus, with the use of conventional indicator tubes, the result of measurement is known instantly, after the measuring operation, for example, due to a coloration readable on a scale. Sampling tubes, however, require a later analysis. This analysis is made at a properly equipped location, usually in a laboratory. In order to obtain a valid result of measurement, the sampling tubes, opened at the location where the sample was taken, must be closed again for transportation to the laboratory, etc.

A prior art sampling tube, employed for testing air for organic compounds, accommodates an activated carbon filler. Until the actual use, the tube is closed by molten glass-sealed tips. For use, the sampling tube is separated from a magazine string of tubes. The tips are opened, and the necessary sample volume is drawn into the tube by suction. The organic compound content of the air is thus adsorbed on the activated carbon. At the end of the sampling operation, the sampling tube is closed with polyethylene caps and sent to a laboratory for analysis of the content of the tube. The handling of a plurality of loosely packaged sampling tubes upon their removal, i.e., closing, keeping track of the samples, and shipping disadvantageously depends to a too large extent, on the skill of the sampler. The need for a remedy is apparent (Drager Bulletin 315, Sept.–Dec.'79, pp 12–15).

SUMMARY OF THE INVENTION

The invention is directed to an as simple as possible packaging, mechanical checking of the association of caps and samples, and reliable shipping to the laboratory of the tubes.

Accordingly, it is an object of the invention to provide an improved sampling tube arrangement of the type having an elongated sampling tube with closing caps made of an elastic plastic adapted to be received upon and close the ends of the sampling tube in which a plurality of caps are joined one to another through webs connecting adjacent closing caps to form a string of closing caps, each of the webs being separable between adjacent closing caps, and further provided with reconnecting means for reconnecting two adjacent closing caps to each other, wherein the reconnecting means includes a plug-in connection comprising a male part provided on one side of the closing cap and a fitting female part on the other side of the closing cap, and each cap having an area immediate the sides for labeling. The webs are preferably provided with indentations for facilitating severance between adjacent caps. In accordance with the preferred embodiment of the invention, the plug-in connection comprises a dovetail male part and a dovetail female part.

The inventive arrangement enables the manufacturer of sampling tubes to deliver the tubes in closed packages of cap strings. To perform the sampling operation, the sampler removes a sampling tube after taking the sample, closes the tube with the caps torn off of the string. The caps may then be labeled with the measuring data on their face.

The plug-in connection between the closing caps makes it possible to join a plurality of sampling tubes into a compact unit for shipping. The inventive design and arrangement of the closing caps ensure a simple packaging, mechanical association of the caps with the samples, and proper shipping to the laboratory. The dovetail shape is a well known and proved design of a plug-in connection.

It is a further object of the invention to provide an improved sampling tube arrangement which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the Drawings:

FIG. 1 shown sampling tubes kept by means of closing caps;

FIG. 2 is a top view of a string of closing caps of FIG. 1;

FIG. 3 is a bottom view of a string of closing caps of FIG. 1; and

FIG. 4 shows sampling tubes closed after taking the sample and ready for shipping.

DETAILED DESCRIPTION

Sampling tubes 1 are stored and shipped in closing cap strips 2 containing, for example, ten pieces each with the caps 3 being joined to each other. Strips 2 are made of a tough elastic material, such as polyethylene, in an injection molding operation. The individual caps 3 are connected to one another by easily breaking webs 4. The breaking at these locations is facilitated by indentations 8.

To obtain shipping packages after taking the samples, closing caps 3 can again be connected to one another by dovetail elements. For this purpose, each closing cap comprises a dovetail male portion 5 on one side and a fitting dovetail female portion 6 on its other side.

FIG. 1 shows a shipping unit with closed sampling tubes 1 received in closing cap strips 2, with the webs 4 being still unbroken. FIG. 2 clearly illustrates the dovetail elements 5,6, and FIG. 3 shows that a labeling area 7 is provided on the underside of caps 3 where identifying information can be provided.

FIG. 4 shows how sampling tubes 1 after taking the samples are closed by caps 3 which are then connected to each other to secure the unit for shipping to the laboratory.

Thus, in accordance with the invention, a sampling tube is provided with closing caps made of an elastic plastic, characterized in that a plurality of closing caps 3 are joined to one another through webs 4 of separation to a string 2 of closing caps and that upon severing the webs 4, two adjacent closing caps 3 can be reconnected to each other by a plug-in connection comprising a male part provided on one side and a fitting female part provided on the other side of a cap, while an area 7 for labeling is provided on the underside of the cap. The webs 4 are provided with indentations. In accordance with the preferred embodiment, the plug-in connection comprises a dovetail male part 5 and a dovetail female part 6.

Hence, the invention provides means for readily reconnecting the tubes in an orderly manner, in series, after the sampling has been completed and after the ends of the elongated tubes have been capped.

While a specific embodiment of the invention has been shown and described in detail to illustrate the application of the principles of the invention, it will be understood that the invention may be embodied otherwise without departing from such principles.

What is claimed is:

1. An improved sampling tube arrangement of the type having an elongated sampling tube with closing caps made of an elastic plastic adapted to be received upon and close the ends of the sampling tube, comprising a plurality of the closing caps, webs connecting adjacent closing caps to form a string of closing caps, each of said webs being severable between adjacent closing caps, reconnecting means for reconnecting two adjacent closing caps to each other, said reconnecting means including a plug-in connection comprising a male part provided on one side of the closing cap and a fitting female part adapted to fittingly receive the male part of an adjacent connecting cap provided on the other side of the closing cap, and each cap having an area intermediate said sides for labeling.

2. An improved sampling tube arrangement as set forth in claim 1, wherein each of the webs includes indentations for facilitating severance of the webs intermediate adjacent closing caps.

3. An improved sampling tube arrangement as set forth in claim 1 or 2, wherein said plug-in connection comprises a dovetail male part and a dovetail female part.

* * * * *